United States Patent [19]

Salim

[11] Patent Number: 4,945,094

[45] Date of Patent: Jul. 31, 1990

[54] SYNERGISTIC BIOLOGICALLY ACTIVE SUBSTANCES

[76] Inventor: Aws S. M. Salim, Department of Surgery, Royal Infirmary, Perth, PH1 1NX, Scotland

[21] Appl. No.: 151,220

[22] Filed: Feb. 1, 1988

[51] Int. Cl.⁵ .............................................. A61K 31/52
[52] U.S. Cl. .................................. 514/264; 514/307; 514/537; 514/708
[58] Field of Search ............... 514/535, 536, 537, 562, 514/708, 880, 925, 264, 307

[56] References Cited

U.S. PATENT DOCUMENTS

| | | | |
|---|---|---|---|
| 3,678,156 | 7/1972 | MacMillan et al. | 426/68 |
| 3,849,576 | 11/1974 | Kalopissis | 514/562 X |
| 3,968,245 | 7/1976 | Higuchi | 514/649 X |

OTHER PUBLICATIONS

British National Formulary, No. 4, 1982, p. 360.

*Primary Examiner*—Leonard Schenkman
*Attorney, Agent, or Firm*—Arnold, White & Durkee

[57] ABSTRACT

The present invention relates to a combination for use in improving the condition of skin and/or mucosa, especially gastro-intestinal mucosa which combination comprises procaine and a physiologically acceptable, organic, in vivo sulphydryl group releasing agent.

Application of a combination of the invention to skin and/or mucosa can improve the condition thereof in a number of ways including increasing its resistance to non-mechanical injury and to degeneration and increasing regeneration as for example in wound healing and skin graft taking.

15 Claims, No Drawings

SYNERGISTIC BIOLOGICALLY ACTIVE SUBSTANCES

The present invention relates to the improvement of skin condition.

Although there is an extensive range of products available in the cosmetic market which allegedly improve skin condition these generally comprise merely barrier and/or moisturising creams which do little more than attempt to control oil and/or water balance in the skin either by creating a barrier to transfer across the skin or by attempting to restore excessive loss from the skin. Thus such products do little if anything to improve the functioning of the skin—especially in relation to resistance to and/or recovery from injury and/or degeneration.

It is an object of the present invention to avoid or minimise one or more of the above disadvantages.

The present invention provides a combination for use in improving the condition of skin and/or mucosa, especially gastro-intestinal mucosa which combination comprises procaine and a physiologically acceptable, organic, in vivo sulphydryl group releasing agent.

Preferred agents of the invention include cysteine, cysteamine, cystine, dimethylsulphoxide, methionine wherein the carboxyl group has been esterified, preferably by lower alkyl having 1 to 6 carbon atoms e.g. methyl, S-methyl substituted, ternary sulphonium, derivatives of methionine such as methionine - S - methyl sulfonium bromide, iodide and chloride (conveniently referred to herein as MMSBr, MMSI and MMSC respectively), and dithioglycerol (also known as British anti-lewisite usually abbreviated to BAL).

It will be noted that at least some of the abovementioned compounds have one or more optically active centres, in particular in the case of the amino acids at the amino - and carboxyl - substituted carbon. For the avoidance of doubt therefore it is observed that the present invention extends to both individual isomers such as D- and L- isomers and enantiomers, and, in the case where two or more optically active centres are present, diastereoisomers, as well as mixtures of isomers including racemic DL mixtures.

In accordance with the present invention the application of a combination of the invention to skin and/or mucosa has been found to improve condition in a number of ways including improved healing of wounds and ulcers (both internally and externally—varicose ulcers on the one hand and peptic ulcers on the other hand), and protection against non-mechanical injury e.g. from injurious chemical materials, and against degeneration from other causes including ageing. The improved condition can also include maintenance of vitality and improved skin graft taking in the case of both attached or free and partial or full thickness grafts. Furthermore procaine has been found to block vagal nerve impulses, inhibit vagal secretory patterns and suppress gastric acid secretion thereby further enhancing the improvement of gastro-intestinal mucosa condition reducing stress ulceration. Moreover the combinations of the invention have been found to exhibit a greater or lesser degree of synergism that is the combinations are more active than the sum of the activities of the components of the combinations when used individually.

In at least some types of premature hair loss inter alia application of procaine to the scalp has moreover been found to reduce or arrest hair loss and/or stimulate new hair growth from hair follicles whose function had previously been impaired but are not yet dead Other beneficial effects that can contribute to the abovementioned beneficial actions of the combinations of the invention which contain procaine are the antispasmodic effects on smooth muscle and analgesic effects in relation to organic or visceral abdominal pain via blockade of neurologic transmission of impulses by procaine.

Advantageously the combinations of the invention include a xanthine, preferably one selected from theophylline, theobromine, aminophylline, ephidrine, and caffeine, most preferably caffeine. In this case there is obtained an enhanced activity whereby the skin condition is further improved to the extent that dermatitis and allergic conditions can be arrested and even reduced.

Advantageously there is also included a vasodilator such as for example menthol in order to further increase the effectiveness of the combinations of the invention in the skin.

Advantageously also there may be included an anti-ischaemic substance and in particular papaverine, and/or an anti-cholinergic and/or vagal nerve blocking substance, especially one or more compounds selected from propoxycaine and amethocaine.

In a further aspect the present invention provides a combination of the invention in intimate admixture with a physiologically acceptable carrier therefor for use in improving the condition of skin and/or mucosa.

In another aspect the present invention provides a topical formulation comprising a combination of the invention in intimate admixture with a pharmaceutically acceptable vehicle therefor. The vehicle should be 'acceptable' in the sense of being generally non-deleterious to the skin of the subject being treated and compatible with the other ingredients of the formulation. It will of course be appreciated that certain individuals have significantly more sensitive skins than the average and that in these special cases alternative vehicles to those normally used may need to be tried.

Suitable vehicles are well known in the art being noted for example in such standard works as the British Pharmacopoeia and the British National Formulary and include ointment bases and cream bases as well as lotions, pastes, jellies, sprays, aerosols and bath oils. Ointments and creams may contain oleaginous absorption colloidal clays, thickening agents such as gum tragacanth or sodium alginate and other pharmaceutically acceptable accessory ingredients such as humectants, preservatives, buffers and antioxidants which have utility in such formulations.

In general cream formulations are preferred as being most acceptable to the majority of users. A particularly convenient base is one utilizing cetomacrogol, comprising for example 30% w/v cetomacrogol emulsifying ointment (30% w/v cetomacrogol emulsifying wax, 20% w/v liquid paraffin wax, 50% white soft paraffin) in freshly boiled and cooled purified water with for example 0.1% w/v chlorocresol or 0.08% w/v propyl hydroxybenzoate, 0 15% w/v methyl hydroxybenzoate and, 1.5% w/v benzyl alcohol.

In general the topical formulations of the invention contain at least 0.5% w/w of procaine, preferably from 1 to 30% w/w, and most preferably from 2 to 10% e.g. 5% w/w of procaine and at least 0.1 % w/w, preferably from 1 to 30 % w/w of a said agent of the invention. Where caffeine is included this is generally used in an amount of from 1 to 30% w/w.

In addition the combinations of the invention (optionally with other active ingredients and/or a suitable vehicle) can be administered orally or parenterally, in particular by intramuscular injection.

For oral administration the combinations of the invention and any accompanying material may be presented as a draught in water or in a syrup, in capsules, cachets, boluses or tablets, as an aqueous or oleaginous solution or suspension or in suspension in a syrup, such suspensions optionally including suspending agents or as an oil-in-water or water-in-oil emulsion. Where desirable or necessary flavouring, sweetening, preserving, thickening or emulsifying agents may be included in the formulation. Tablets may contain the combinations of the invention and any accompanying material as a powder or granules optionally mixed with binders, lubricants, inert diluents or surface-active or dispersing agents.

For parenteral administration the combinations of the invention and any accompanying material may be presented in sterile solutions of suspensions in aqueous or oleaginous vehicles, which may also contain preservatives and material for rendering the solution or suspension isotonic with the blood of the intended recipient. Such formulations may conveniently be presented in unit-dose or multi-dose sealed containers.

For administration orally in liquid form or parenterally the combinations of the invention are preferably presented in solution or suspension or emulsion at a concentration of from 0.5 to 15% more preferably 2 to 5% w/v in unit multidose form. When presented in unit dose form each unit dose preferably contains from 50 to 500 mg of procaine.

In general for the purposes of treating gastrointestinal mucosa the procaine is administered at a dosage rate of from 35 to 140 mg/kg of subject bodyweight per day, preferably from 60 to 80 mg/kg/day whilst the agents of the invention are administered at a dosage rate of from 10 to 100 mg/kg bodyweight per day, preferably from 15 to 35 mg/kg/day. The dosage may be administered in one or more doses per day and preferably is administered at intervals of from 2 to 6 hours, most preferably every 4 hours. Advantageously the combinations of the invention are administered in a slow release or sustained release vehicle, various suitable vehicles of this type being known in the art.

Where papaverine is included this is generally used at a dosage rate of the order of 1 mg/kg/day.

The present invention also provides a process for producing a pharmaceutical formulation of the invention comprising bringing into intimate association a combination of the invention and a pharmaceutically acceptable vehicle therefor.

Combinations of the invention may be administered to human beings to improve skin condition and the present invention accordingly extends to a method of improving the condition of skin or mucosa comprising administration of an effective dosage of a combination of the invention to the skin or mucosa of a subject.

Where skin is being treated the combination of the invention will normally be applied in the form of a topical formulation of the invention at least once a day, preferably 2 or 3 times a day. The formulation is generally spread over the area to be treated and gently rubbed in.

Where mucosa are being treated, especially the gastrointestinal mucosa, caffeine is preferably not included.

Further preferred features and advantages of the invention will appear from the following detailed examples given by way of illustration only.

EXAMPLE 1

Preparation of cream for treating skin

| | |
|---|---|
| Procaine hydrochloride (anhydrous) | 5 g |
| Caffeine hydrate | 2 g |
| Methylmethionine sulfonium chloride | 2 g |
| L-Cysteine hydrochloride | 2 g |
| Menthol crystals | 1 g |
| Cetomacrogol 'A' (B.P.) | add to 100 g |

The formula is prepared in a medium of 25° C. temperature 5 g procaine hydrochloride is mixed with 2 g of caffeine in a glass or stainless steel container and 88 g cetomacrogol 'A' is added and mixed for 10 minutes. After standing for 30 minutes 2 g of each of methylmethionine sulfonium chloride and cysteine hydrochloride are added and mixed together for 10 minutes and then allowed to stand for 30 minutes. 1 g of menthol crystals finely ground is then added and mixed for 10 minutes. The mixture is then placed into an airtight opaque (non-transparent) glass container and store at a temperature not exceeding 26° C. No direct light should be projected at the container during the preparation which was carried out at approximately 25° C. After preparation formula should not be used for at least 12 hours, should not be left exposed to the air for long periods, and should not be directly exposed to the sun.

EXAMPLE 2

Use of Topical Cream

The cream of Example 1 was applied once daily, in the evening, in a convenient amount onto the part of the skin to be treated. The skin was washed the following morning with warm water with or without soap. Treatment may be for a few days or weeks depending on each case, the individual's existing skin condition and requirements. For protection against sun irritation the daily application is limited to the period of exposure. As a beauty cream, the cream is applied one daily for 4 weeks then once or twice weekly (depending on the case) for as long as desired. For treatment of keratosis or house wife dermatitis, daily application for four weeks is recommended.

Example 3

Detailed Evaluation of Activity of Topical Cream

All trials were conducted by the double blind method and the cream of Example 1 was investigated against cetomacrogol 'A' cream (B.P.) free of any other ingredients as a control In a group of females (n=26) with an age range of 18-29 yrs and a history of skin erythema, itching and scaling following prolonged exposure to the sun (average exposure 5 days) during the summer, daily topical application of the formula to skin parts exposed to this irritation commencing the evening before exposure and on every evening during the exposure period completely protected the skin against all previously experienced adverse effects of this exposure. Age and sex matched controls (n-11) of a similar history had no protection against sunlight exposure effects.

(2) Application of the formula once daily for four weeks by a group of males and females (n-41, age range 56-61yrs) so as to treat hyperkeratotic lesions of the face and upper limbs caused complete shedding of lesions and replacement by skin similar to that of its neighbourhood in all cases. Lesions were observed to fall off healthy skin underneath demostating simulation of skin repair and renewal. A similar group of males and females (n=12, age range 52-59yrs) acting as controls had no beneficial effects as to their lesions after using cetomacrogol 'A' cream similarly.

(3) Twenty seven females of an age range 39-53yrs complaining of house wife dermatitis (rough, thick and fissured skin) of the hands were treated with the formula (once daily application to the affected areas of skin) for six weeks. Twenty two females were completely satisfied with the treatment and had smooth and completely intact skin at the end of the treatment period. They were then instructed to use the formula twice weekly for as long as desired. Twenty of these females were followed up for six months and were not observed to re-develop any degree of house wife dermatitis. The other five females of the original 27 were not completely satisfied with the treatment after six weeks, however, they expressed desire to continue using their treatment and were, therefore, instructed to do so twice weekly for as long as desired. All these five females were completely satisfied with the results of their treatment after 9-12 weeks of first using it. They were followed up for six months and were not observed to re-develop any of their previous signs or symptoms. A similar group of females (n=9, age range 48-53yrs) were similarly treated with cetomacrogol 'A' cream for six weeks, however, none of them expressed any satisfaction nor were there any signs of improvement as to their dermatitis.

(4) Sixty three females, age range 8-25yrs, used the formula as a beauty cream daily for six weeks. None had any history of skin allergy or diseases and all were using some form of a beauty cream on the market so as to keep their skin "smooth and moist". At the end of the six week period 51 females (81%) preferred the formula to their previous cream and stated maximum benefit in terms of a smoother and firmer skin compared to pre-treatment. On the other hand, none of 27 control females (age range 17-24yrs) with no previous history of skin allergy or diseases were satisfied with their treatment and expressed no desire to substitute it for their original cream of preference.

(5) Thirty nine females (age range 43-57yrs) with signs of damage due to skin ageing on face and limbs (loss of smoothness, loss of firmness, hyperkeratosis) were observed to develop smooth and firm skin after six weeks of daily use of the formula. They were instituted on a twice weekly treatment for 18 months. Upon follow up, signs of skin damage at treatment sites were not observed to re-develop. Controls (n=31, age range 53-57yrs) demonstrated no response to their treatment after six weeks and they were not treated any longer.

(6) Sixteen females of an age range 47-54yrs with facial wrinkles were carefully assessed as to the severity and extent of these wrinkles which were then carefully maped on special charts. All females were instituted on a six weeks daily treatment followed by twice weekly treatment for 22 months. After 3 months of treatment all cases demonstrated significant improvement of their wrinkles in terms of severity. Facial skin was observed to be smoother and firmer than before treatment, which is probably the major factor behind the wrinkles becoming less apparent. At the end of the nearly two years study no new wrinkles were observed to have developed and the original wrinkles were almost invisible. Eighty seven per cent (14 cases) of those patients significantly improved as to the severity of their wrinkles after 6 weeks of treatment whereas none of the controls (n=9, age 43-51 yrs) demonstrated any improvement after a similar period of treatment and were not treated any longer. Example 4

Detailed Evaluation of MMSBr + Procaine

All trials were conducted by the double blind method using a topical cream constituted as follows:

| MMSBr | 2 g |
|---|---|
| Procaine HCl (anhydrous) | 5 g |
| Cetomacrogol 'A' (B.P.) | add to 100 |

The cream was prepared by a similar procedure to that in Example 1 and investigated against cetomacrogol 'A' cream (B.P.) free of any other ingredients as a control.

1. Twenty-one females, age range 21-32 yrs, of no previous history of any dermatological disease or disturbance and using a market beauty cream to maintain a smooth or moist skin were instituted on a once daily application of the formula for six weeks as a substitute to their original beauty cream. After treatment 18 females (86%) preferred the formula to their original cream and stated that their skin was smoother, firmer and less irritated by prolonged exposure to the sun.

None of the control females (n=12, age range 19-26 yrs) expressed any benefit from their cream and did not wish to substitute it for their original cream of preference. It is, thus, demonstrated that this formula is a suitable and convenient beauty cream.

2. Eighteen females of an age range 52-58 yrs with obvious dermatological signs of ageing (loss of firmness, roughening, keratosis, wrinkles) of face and limbs were instituted on a once daily treatment for six months. Similarly, a control group of 9 females of an age range 47-53 yrs were used as controls. After 8 weeks of treatment all members of the treatment group were observed to have acquired smoother skin and by six months time they were significantly improved with almost non-visible degenerative changes and a smooth firm skin texture. They were instructed to use the formula twice weekly for another 12 months during which no observed obvious signs of skin ageing or degeneration developed. Controls demonstrated no benefit from their treatment.

3. Fourteen females of an age range 18-36 yrs and a history of intolerance to exposure to the sun for an average period of 3 days with subsequent development of erythema and scaling using the formula the night before and on every day during exposure completely protected the skin against any signs of sunlight irritation and burn. The six female controls (age range 26-31 yrs) of similar history and course of treatment with the formula vehicle only had no protection against sunlight-induced irritation and burn. The control group was then used to investigate the therapeutic potency of the formula in cases of mild burns. All six females were instituted on a twice daily application of the formula for seven days. Twenty four hours after commencing treatment all patients were free of itching and discomfort. On the 3rd day erythema completely disappeared and on the 4th day there were no signs of erythema or scaling.

EXAMPLES 5-8

Preparation of Capsules for Gastro-intestinal (G.I.) Treatment

The following compositions were prepared in a glass container screened off from any direct light and at a room temperature of 26° C. by mixing the ingredients (all in powder form) and then filling the required amount into gelatinous capsules. These were then stored in opaque containers away from direct light and at a room temperature of 26° C. All capsules were used within six months of preparation.

EXAMPLE 5

Preparation and Use of G.I. Composition

| | | |
|---|---|---|
| Procaine hydrochloride | 500 mg | each Capsule |
| MMSC | 500 mg | |
| Cysteine | 100 mg | |

Twelve males of an average age 41 yrs with symptomatic and endoscopic duodenal ulceration were instituted on one capsule at six hourly intervals for 6 weeks. Symptoms in all patients were completely controlled within 12 hours and then all patients were tolerant of their original diet till the end of the treatment period and by the end of which all patients had completely healed ulcers.

This formula has a significantly better healing potency than procaine alone given in a dose of 1 g four times a day.

EXAMPLE 6

Preparation and Use of G.I. Composition

| | | |
|---|---|---|
| Procaine hydrochloride | 500 mg | each Capsule |
| MMSC | 500 mg | |
| Cysteine | 200 mg | |
| Papaverine | 10 mg | |

Ten male adults of an average age 32 yrs with a long history of not less than one year of relapses and remissions of duodenal peptic ulceration symptoms and endoscopically confirmed ulceration at presentation were instituted on one capsule 6 hourly for six weeks. In all subjects symptoms were immediately controlled and ulcers completely healed by four weeks. Seven control males of an average age 42 yrs and a similar history and confirmed ulceration at presentation had no symptomatic relief with placebo 1 g six hourly for four weeks and none of the ulcers were healed during this period. In both groups no dietary restriction was introduced. The formula treatment group was then instituted on one capsule 12 hourly for six months then one capsule at bedtime daily for another six months. No patient had any symptomatic relapse during the one year follow-up and endoscopy at both 6 months and a year after healing showed no recurrence. This composition was thus found to be faster acting than that of Example 5.

EXAMPLE 7

Preparation and Use of G.I Composition

Each gelatin capsule contained:

| | |
|---|---|
| Procaine Hydrochloride | 500 mg |
| Amethocaine Hydrochloride | 500 mg |
| Amethocaine Hydrochloride | 30 mg |
| Propoxycaine Hydrochloride | 30 mg |
| MMSBr | 500 mg |

In 23 males of an age range 29-37 yrs and symptomatic and endoscopic duodenitis were instituted on one capsule six hourly for six weeks with no dietary restrictions. Symptoms were immediately controlled and no signs of duodenitis were observed at endoscopy after six weeks.

This composition has been found to be significantly more potent than each of its main components in terms of the rapidity of symptoms control and healing efficacy when used in the abovementioned manner when compared with the doses of the individual components required to achieve a similar effect.

Example 8

Preparation and Use of G.I. Composition

Each gelatin capsule contained:

| | |
|---|---|
| Procaine hydrochloride | 500 mg |
| Amethocaine hydrochloride | 30 mg |
| Propoxycaine hydrochloride | 30 mg |
| MMSB | 500 mg |
| Cysteine | 100 mg |
| Papaverine | 10 mg |

1. Forty-seven males and females (age range 28-45 yrs) with a one month or less history of symptoms of duodenal ulceration and duodenitis endoscopically observed at presentation were instituted on one capsule at six hourly intervals with no dietary restriction. Symptoms in all cases were immediately controlled and no duodenitis was observed endoscopically after 4 weeks of treatment.

2. Eighteen male and female patients of an age range 29-52 yrs with a 3 month or less history of classical duodenal ulceration symptoms and frank ulceration endoscopically were instituted on one capsule six hourly for four weeks then one capsule at bedtime for 12 months without any dietary restrictions. A sex and age matched group (n=7) was similarly given placebo for four weeks so as to act as controls. The group using the formula had symptomatic relief immediately and complete healing of their ulceration within four weeks and no relapses symptomatically or andoscopically (at 6 and 12 months) in all cases. None of the controls had symptomatic relief or healing up to four weeks of using the placebo.

This formula is therefore significantly better than its individual components for symptomatic control and healing of duodenitis and duodenal ulceration. It is not intended that the following observation should in any way restrict the scope of the present invention but it is believed that the efficacy of the composition is due in part to the production of a medical vagotomy so as to maintain mucosal blood flow and suppress acid secretion.

EXAMPLE 9

Enhancement of Restoration of Hair Growth

It has previously been observed that the topical application of castor oil to areas of human scalp suffering from hair loss can reduce such hair loss. In accordance with the present invention there is now provided a method of treating human scalp suffering from hair loss so as to prevent hair loss and restore hair growth using a combination comprising procaine, a physiologically acceptable, organic, in vivo sulphydryl group releasing agent, and castor oil, as well as such a combination.

These further aspects of the invention are illustrated by the following:

In a controlled double blind study the product

| Procaine hydrochloride (Anhydrous) | 5 g |
| Caffeine hydrate | 2 g |
| Cysteine hydrochloride | 2 g |
| Methylmethionine sulfonium chloride | 2 g |
| Menthol crystals | 1 g |
| Castor oil B.P. | 100 ml | was prepared as described earlier and topically applied overnight by 25 healthy male volunteers of an age between 25-32 years and suffering from excessive hair loss. After four months, 18 subjects were completely satisfied with their treatment and were not experiencing any hair loss. After six months of commencing treatment, all 25 subjects were fully controlled as to hair loss and in 21 cases growth of new hair was visible at the hair line.

In the control group there were 10 males of an age between 28-36 years complaining of excessive hair loss. They received castor oil once daily application to the scalp overnight. After six months of treatment, four subjects had their hair loss controlled. However, they had no visible new hair growth.

The treatment group was then instituted on a twice weekly course for 18 months. During this period hair was not lost and its growth was restored in areas of the scalp not previously bald. In those subjects with bald patches, growth of hair was clearly visible adjacent to the receding hair line. There were no adverse reactions or allergic effects in any treatment case during the two years course.

It was concluded that this treatment affords advantages over castor oil alone, and provides an actual preventive therapy to hair loss in addition to stimulating growth of new hair from apparently bald parts of the scalp. In this latter case, it appears that these bald patches have follicles which are not yet dead and can be activated to regain their biological functions.

Example 10

Composition for use in treatment of intestinal inflammation.

Capsules were prepared, each containing:

| Procaine HCl | 500 mg |
| Caffeine hydrate | 50 mg |
| MMSC | 500 mg |
| Cysteine | 200 mg |
| with or without papaverine (50 mg) and similarly by substituting MMSBr for MMSC. | |

Reduction of symptoms was found in relation to abdominal pain and diarrhea caused by chronic non-specific intestinal inflammation (i.e. Crohn's disease and ulcerative colitis). In addition the composition is very potent in the treatment of irritable bowel cases.

Example 11

Toxicity Studies on combination of Invention

A. Preparation of Combination 5 g of procaine were dissolved in 100 ml of double distilled water then 2 g caffeine hydrate were added. To this colourless and transparent solution 2 g of each of L-Cysteine hydrochloride and methylmethionine sulfonium chloride and 1 g of menthol crystals were added. Similar preparations of double and triple strength were also made. In each case a colourless transparent solution was obtained.

B. Animal Tests

Six groups of ten male and female Sprague-Dawley rats weighing between 200-250 g were denied solid food for 24 hours before study. One ml of each of the combination preparations was administered intraperitoneally into the left iliac fossa of an experimental group. Members of each of the remaining three groups received, under light ether anaesthesia and by orogastric instillation into the stomach, one ml of one of the combination preparations.

RESULTS

Animals were observed for 24 hours then allowed food and observed for another six days. There were no deaths among the groups and no discomfort, excitation, withdrawal, drowsiness, vomitting or diarrhea was observed in any case.

It is, therefore, observed that up to four mls of a triple concentration of the formula per kg body weight is not associated with any observed adverse effects concluding that the formula is particularly safe for topical use.

EXAMPLE 12

Clinical Trials

All studies were conducted on the compositions of Example 1 against cetomacrogol B.P. in a double blind way.

1. In 21 paraplegic males and females of an age between 43-61 years, the twice daily application of the formula in liberal amounts to the buttock and lower limbs with regular physiotherapy completely prevented the development of pressure ulceration during the six weeks treatment course. However, there were three ulceration cases in the control group (10 males and females of an age range 51-59 years).

2. The ulceration cases in the control group above were treated with twice daily application of the formula After 18 days all three ulcerations were completely healed 3. Fourteen females of an age range 48-61 years were observed to complain of itching with obvious skin erythema in the skin surrounding basal and squamous cell carcinoma of the face and limbs after first course radiotherapy treatment. Within 48 hours of twice daily application of the formula to the tumour neighbourhood all complaints were relieved and erythema disappeared. Continuation of therapy completely prevented the development of these effects with the rest of radiotherapy courses. Controls, six females with similar conditions and complaints of an age 61-64 years, obtained no relief with their treatment which was similarly instituted.

4. Thirty seven females of an age 38-54 years, complaining of itching, scaling and oozing of the skin of the lower third of the medial side of the leg covering incompetent venous perforators associated with varicosity of the long saphenous vein, were instituted on twice daily application of the formula for 4 weeks with foot elevation at night. In all cases, signs and symptoms of varicose dermatitis were completely relieved. Application of the formula base with foot elevation at night to a group of 7 females of an age range 34–41 years with a similar condition and complaint brought relief of symptoms and signs to one patient only.

5. Eight males and females of an age range 49–57 years with varicose ulceration of the skin over the lower third of the medial side of the leg were treated with the formula after drying the ulcer with magnesium sulfate powder. The formula was twice daily applied to the ulceration and its surrounding skin for six weeks and elastic stockings were also used. Initially, patients were confined to complete bed rest with foot elevation for 3 weeks then allowed walking with elevation of the foot overnight. There were five male and female controls of an age range 43 - 62 years with the same condition which were similarly treated with the formula base instead. In six treatment subjects the ulceration was completely healed within four weeks and in the remaining two treatment cases it completely healed within six weeks. Controls obtained no healing with their treatment.

6. Following primary excision and suturing of traumatic wounds of the limbs in 47 males (age 14–39 years) the formula was applied twice daily with conventional dressing for ten days. Complete healing of these wounds was then observed and upon six months' follow-up there were no cases of dehiscence, hypertrophic scarring or pigmentation of the surrounding skin. There were 27 male controls (age 21–36 years) of comparable traumatic wounds. Treatment by similar excision and application of the base only resulted in 20 cases of satisfactory wound healing but in 7 cases hypertrophic scarring developed in the follow-up period.

7. Twenty three males and females (age 11–26 years) with 3rd degree burns of the limbs of an area 9 were instituted on twice daily application of the formula to the burn area and were compared to a control group of 15 males and females (age 15–37) years) with similar burns treated by twice daily application of the formula base. Treatment in both groups was for 3 weeks. In the treatment cases the burns were observed to heal in a significantly better way than controls. The parameters of comparison were: pain or discomfort, itching, pigmentation and discolouration.

8. Following excision and partial thickness skin grafting in cases of burns of the limbs of an area of 9, ten male and female subjects (age 14–21 years) had an application of a liberal amount of the formula over the graft before dressing and 12 male and female controls (age 10–19 years) were similarly treated with the formula base When the dressing was removed on the 5th postoperative day, all treatment subjects had a successful skin graft taking but this failed in four controls.

What is claimed is:

1. A combination for use in improving the condition of skin, which combination comprises a xanthene and procaine and a physiologically acceptable, organic, in vivo sulphydryl group releasing agent selected from the group consisting of cysteine, cysteamine, cystine, dimethylsulphonxide, methionine wherein the carboxyl group has been esterified, s-methyl substituted ternary sulphonium, derivatives of methionine and dithioglycerol wherein said procaine and said agent are present in relative proportions 2. A combination for use in improving the condition of skin, which combination comprises a xanthene selected from theophylline, theobromine, aminophylline, ephedrine, and caffeine and procaine and a physiologically acceptable, organic, in vivo sulphydryl group releasing agent selected from the group consisting of cysteine, cysteamine, cystine, dimethylsulphoxide, methionine wherein the carboxyl group has been esterified, s-methyl substituted ternary sulphonium, derivatives of methionine and dithioglycerol wherein said procaine and said agent are present in relative proportions of from 1:30 to 30:1 by weight.

3. A combination for use in improving the condition of skin, which combination comprises a vasodilator and procaine and a physiologically acceptable, organic, in vivo sulphydryl group releasing agent selected from the group consisting of cysteine, cysteamine, cystine, dimethylsulphoxide, methionine wherein the carboxyl group has been esterified, s-methyl substituted ternary sulphonium, derivatives of methionine and dithioglycerol wherein said procaine and said agent are present in relative proportions of from 1:30 to 30:1 by weight.

4. A combination for use in improving the condition of skin, which combination comprises methanol and procaine and a physiologically acceptable, organic, in vivo sulphydryl group releasing agent selected from the group consisting of cysteine, cysteamine, cystine, dimethylsulphoxide, methionine wherein the carboxyl group has been esterified, s-methyl substituted ternary sulphonium derivatives of methionine and dithioglycerol wherein said procaine and said agent are present in relative proportions of from 1:30 to 30:1 by weight.

5. A combination as claimed in claim 4 which includes at least one of an anti-ischaemic substance, an anti-cholinergic substance, and a vagal nerve blocking substance.

6. A combination as claimed in claim 5 which includes at least one of papaverine, propoxycaine, and amethocaine.

7. A combination for use in improving the condition of skin, which combination comprises castor oil and procaine and a physiologically acceptable, organic, in vivo sulphydryl group releasing agent selected from the group consisting of cysteine, cysteamine, cystine, dimethylsulphoxide, methionine wherein the carboxyl group has been esterified, s-methyl substituted ternary sulphonium, derivatives of methionine and dithioglycerol wherein said procaine and said agent are present in relative proportions of from 1:30 to 30:1 by weight.

8. A method of improving the functioning of the skin of a human subject in relation to resistance to and recovery from injury and degradation comprising the topical application to the skin of said subject of a composition in intimate admixture with a physiologically acceptable carrier therefor to form of a suitable cosmetic topical formulation, said composition comprising a combination comprising a xanthene and procaine and a physiologically acceptable, organic, in vivo sulphydryl group releasing agent selected from the group consisting of cysteine, cysteamine, cystine, dimethylsulphoxide, methionine wherein the carboxyl group has been esterified, s-methyl substituted ternary sulphonium, derivatives of methionine and dithioglycerol wherein said procaine and said agent are present in relative proportions of from 1:30 to 30:1 by weight.

9. A method of improving the functioning the skin of a human subject in relation to resistance to and recovery from injury and degradation comprising the topical application to the skin of said subject of a composition in intimate admixture with a physiologically acceptable carrier therefor to form of a suitable cosmetic topical formulation, said composition comprising a combination comprising a xanthene and procaine and a physiologically acceptable, organic, in vivo sulphydryl group releasing agent selected from the group consisting of cysteine, cysteamine, cystine, dimethylsulphoxide, methionine wherein the carboxyl group has been esterified, s-methyl substituted ternary sulphonium derivatives of methionine and dithioglycerol wherein said procaine and said agent are present in relative proportions of from 1:30 to 30:1 by weight, wherein said application is repeated several times over a period of several days.

10. A method of treating male human scalp suffering premature hair loss so as to prevent hair loss and restore hair growth using a combination which comprises a xanthene and procaine and a physiologically acceptable, organic, in vivo sulphydryl group releasing agent selected from the group consisting of cystine, cysteamine, cystine, dimethylsulphoxide, methionine wherein the carboxyl group has been esterified, s-methyl substituted ternary sulphonium, derivatives of methionine and dithioglycerol wherein said procaine and said agent are present in relative proportions of from 1:30 to 30:1 by weight.

11. A method of improving the functioning of the mucosa of a mammal in relation to resistance to and recovery from one mucosal injury selected from the group of mucosal injuries consisting of duodenitis, non-specific intestinal inflammation, and irritable bowel comprising the administration of an effective dosage of a combination of procaine and a physiologically acceptable organic, in vivo sulphydryl group releasing agent, to said mammal.

12. A method of treatment or prophylaxis of stress, gastric or peptic ulcers in a mammal comprising the administration of therapeutically or prophylactically effective dosage of a combination of procaine and a physiologically acceptable organic, in vivo sulphydryl group releasing agent, to said mammal in intimate admixture with a physiologically acceptable carrier therefor.

13. A method as claimed in claim 12 wherein said combination is administered at a dosage rate of from 35 to 140 mg/kg of bodyweight of said mammal of procaine and from 10 to 100 mg/kg of bodyweight of said mammal of said physiologically acceptable organic in vivo sulphydryl group releasing agent.

14. A method as claimed in claim 13 wherein said combination is administered orally.

15. A method as claimed in claim 14 wherein said combination is administered in unit dosage form.

* * * * *